United States Patent
Vezzu

(10) Patent No.: US 9,693,897 B2
(45) Date of Patent: Jul. 4, 2017

(54) ULTRASONIC HANDPIECE

(71) Applicant: ALCON RESEARCH, LTD., Fort Worth, TX (US)

(72) Inventor: Guido Vezzu, Pfungen (CH)

(73) Assignee: Alcon Research, Ltd., Fort Worth, TX (US)

( * ) Notice: Subject to any disclaimer, the term of this patent is extended or adjusted under 35 U.S.C. 154(b) by 220 days.

(21) Appl. No.: 14/435,541

(22) PCT Filed: Nov. 20, 2012

(86) PCT No.: PCT/US2012/065997
§ 371 (c)(1),
(2) Date: Apr. 14, 2015

(87) PCT Pub. No.: WO2014/081410
PCT Pub. Date: May 30, 2014

(65) Prior Publication Data
US 2015/0272781 A1    Oct. 1, 2015

(51) Int. Cl.
*A61B 17/32*  (2006.01)
*A61F 9/007*  (2006.01)
*A61G 12/00*  (2006.01)
*A61B 90/00*  (2016.01)

(52) U.S. Cl.
CPC .............. *A61F 9/00745* (2013.01); *A61B 2017/320076* (2013.01); *A61B 2090/0817* (2016.02); *A61G 12/001* (2013.01)

(58) Field of Classification Search
CPC ...... A61F 9/007; A61F 9/00745; A61B 17/30; A61B 17/32; A61B 17/36; A61B 2017/320076; A61B 2017/0046; A61B 2017/00477
See application file for complete search history.

(56) References Cited

U.S. PATENT DOCUMENTS

| | | |
|---|---|---|
| 5,263,957 A | 11/1993 | Davison |
| 6,458,143 B1 | 10/2002 | Sugai |
| 6,497,714 B1 | 12/2002 | Ishikawa et al. |
| 6,761,698 B2 * | 7/2004 | Shibata .......... A61B 17/320068 600/439 |
| 7,588,553 B2 | 9/2009 | Dewey |
| 7,651,490 B2 * | 1/2010 | Boukhny ............ A61F 9/00745 606/1 |
| 7,758,524 B2 | 7/2010 | Barthe et al. |
| 8,016,843 B2 | 9/2011 | Escaf |
| 8,142,460 B2 | 3/2012 | Cotter et al. |
| 2003/0045887 A1 | 3/2003 | Sakurai et al. |

(Continued)

FOREIGN PATENT DOCUMENTS

| | | |
|---|---|---|
| CN | 2235269 Y | 9/1996 |
| JP | 1991-139347 A | 6/1991 |

(Continued)

*Primary Examiner* — Victor Nguyen

(57) ABSTRACT

In certain embodiments, a handpiece system includes an ultrasonic handpiece and a spatula. The ultrasonic handpiece includes a vibration source and a horn. The vibration source is configured to produce ultrasonic vibrations, and a horn is configured to transform the vibrations into ultrasonic motion. The spatula is coupled to the horn and configured to move according to the ultrasonic motion. The spatula may have any suitable shape and size.

13 Claims, 5 Drawing Sheets

(56) References Cited

U.S. PATENT DOCUMENTS

| | | |
|---|---|---|
| 2006/0030797 A1 | 2/2006 | Zhou et al. |
| 2006/0235305 A1 | 10/2006 | Cotter et al. |
| 2007/0060926 A1 | 3/2007 | Escaf |
| 2008/0172076 A1 | 7/2008 | Chon et al. |
| 2009/0030438 A1 | 1/2009 | Stulen |
| 2010/0004667 A1 | 1/2010 | Young et al. |
| 2011/0196286 A1 | 8/2011 | Robertson et al. |
| 2011/0196400 A1 | 8/2011 | Robertson et al. |
| 2011/0196405 A1 | 8/2011 | Dietz |
| 2012/0072197 A1* | 3/2012 | Ovchinnikov ...... A61F 9/00745 703/11 |
| 2012/0143233 A1 | 6/2012 | Sinelnikov |

FOREIGN PATENT DOCUMENTS

| | | |
|---|---|---|
| JP | 2001104326 A | 4/2001 |
| JP | 2003116863 A | 4/2003 |
| JP | 2008508065 A | 3/2008 |
| JP | 2008114066 A | 5/2008 |
| JP | 2009538660 A | 11/2009 |

\* cited by examiner

ULTRASONIC HANDPIECE

CROSS REFERENCE TO RELATED APPLICATIONS

This application is a section 371 national stage phase of International Application No. PCT/US2012/065997 filed Nov. 20, 2012 and titled "ULTRASONIC HANDPIECE" which is hereby incorporated herein by reference in its entirety.

TECHNICAL FIELD

The present disclosure relates generally to ultrasonic devices, and more particularly to ultrasonic handpieces.

BACKGROUND

In certain ocular diseases, such as diabetic retinopathy, heavy membranes and other kinds of connective tissue grow in the posterior segment of the eye and provoke the deterioration of the eye's health. Blood vessels may grow along the retina and vitreous humour. Treatment involves removal of the tissue growth. Without timely treatment, these new blood vessels can bleed, cloud vision, or destroy the retina.

BRIEF SUMMARY

In certain embodiments, a handpiece system comprises an ultrasonic handpiece and a spatula. The ultrasonic handpiece comprises a vibration source and a horn. The vibration source is configured to produce ultrasonic vibrations, and a horn is configured to transform the vibrations into ultrasonic motion. The spatula is coupled to the horn and configured to move according to the ultrasonic motion. The spatula may have any suitable shape and size.

BRIEF DESCRIPTION OF THE DRAWINGS

Exemplary embodiments of the present disclosure will now be described by way of example in greater detail with reference to the attached figures, in which.

DESCRIPTION OF EXAMPLE EMBODIMENTS

Figure 1:
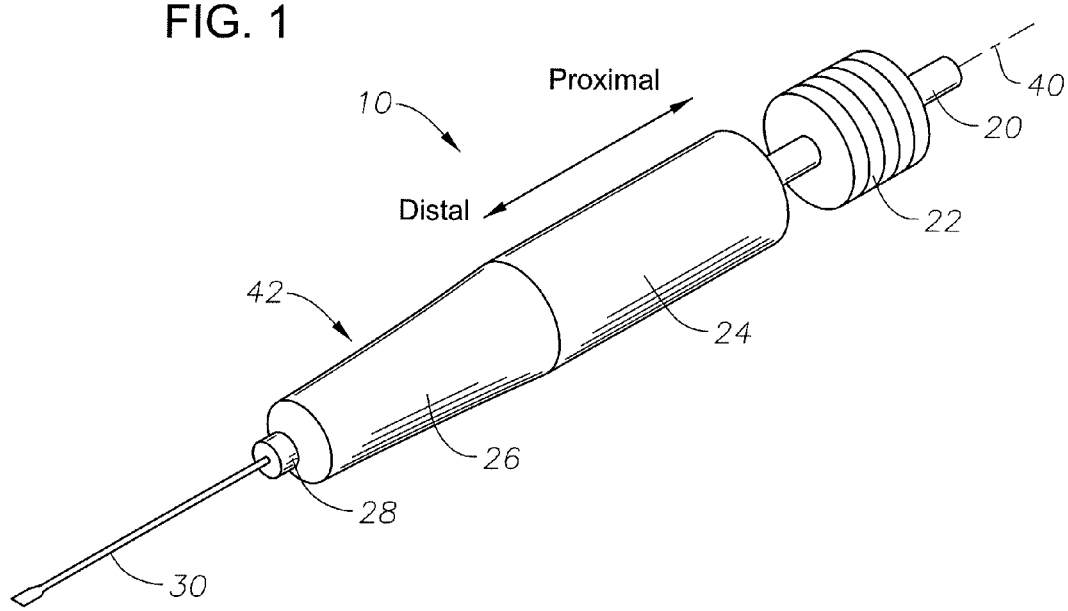
FIG. 1 illustrates an example of an ultrasonic handpiece according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of an ultrasonic handpiece 10. Ultrasonic handpiece 10 may include any suitable components that are configured to move a spatula 30 with ultrasonic motion. Spatula 30 may be used to facilitate separation, dissection, and/or delamination of heavy membranes and/or other connective tissue of the retina in order to treat ocular diseases such as diabetic retinopathy. In the example, ultrasonic handpiece 10 includes a shaft 20, a plug 22, a vibration source 24, a horn 26, a distal portion 28, and a spatula 30 coupled as shown from a proximal end to a distal end along a central axis 40.

Ultrasonic motion occurs with a frequency that is above approximately 20,000 hertz. Ultrasonic motion may occur in any suitable direction. In certain embodiments, ultrasonic motion may include longitudinal and/or torsional motion. Longitudinal motion may be parallel to central axis 40. Torsional motion may rotate about an axis, such as central axis 40.

Vibration source 24 is configured to produce ultrasonic vibrations. Ultrasonic vibrations are vibrations with a frequency above approximately 20,000 hertz. Vibration source 24 may include any suitable components that can produce ultrasonic vibrations. In certain embodiments, a set of piezoelectric crystals may produce ultrasonic vibrations. For example, a first set of piezoelectric crystals is polarized to produce longitudinal motion, and a second set of piezoelectric crystals is polarized to produce torsional motion. Two drive signals may drive the two sets of crystals.

Horn 26 is configured to transform the vibrations generated by vibration source 24 into ultrasonic motion. Horn 26 may include a distal portion 28 that is coupled to spatula 30, and may comprise any suitable material, such as a titanium alloy. In certain embodiments, ring-shaped piezoelectric crystals may be secured to horn 26 such that the crystals may communicate translational and/or torsional motion to horn 26. Distal portion 28 of horn 26 may then communicate the motion to spatula 30, which moves according to the ultrasonic motion. In certain embodiments, vibration source 24 and horn 26 may be disposed within a hollow cylindrical housing 42.

Figure 2A:
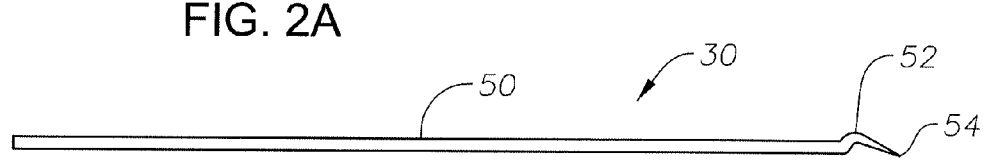
FIGS. 2A through 2F illustrate examples of a spatula of an ultrasonic handpiece according to certain embodiments.
Figure 2B:
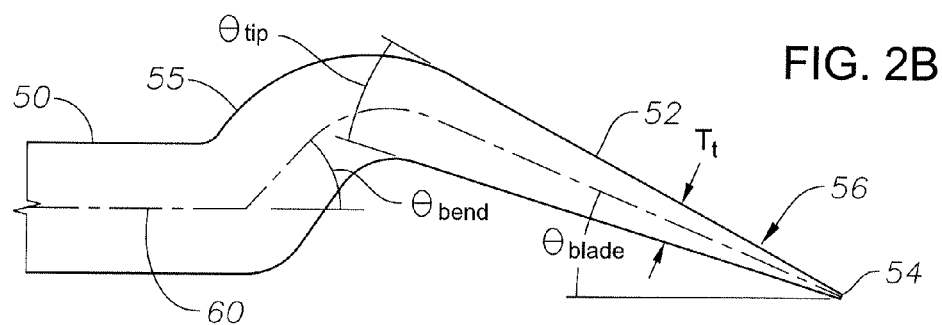
Figure 2C:
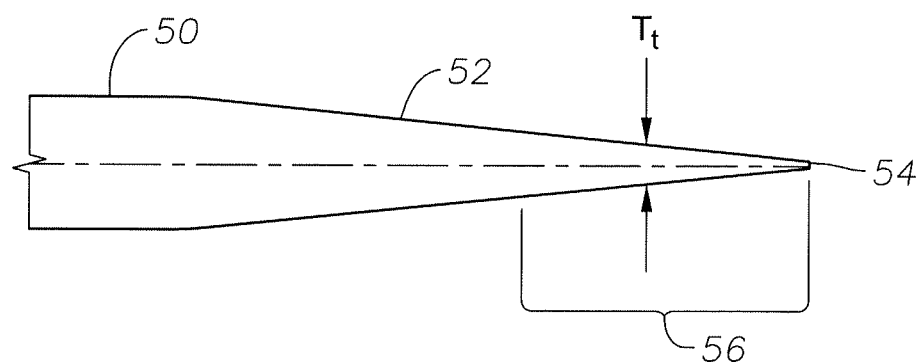
Figure 2D:
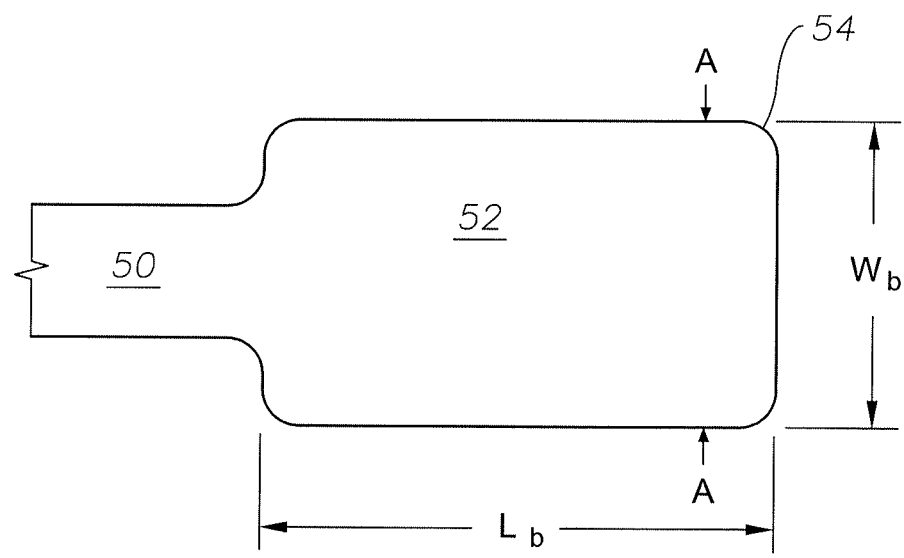

FIGS. 2A through 2F illustrate examples of spatula 30. FIG. 2A is a side view of spatula that includes a spatula handle 50 and a blade 52 with an edge 54. FIG. 2B is a more detailed view of a cross-section of blade 52. Spatula handle 50 has a central axis 60, and blade 52 has a proximal portion 55 and a tip 56. A bend angle $\theta_{bend}$ represents the angle between the central axis 60 and the axis of proximal portion 55. A tip angle $\theta_{tip}$ represents the angle between the surfaces of tip 56. A tip thickness $T_t$ represents the thickness of tip 56. A blade angle $\theta_{blade}$ represents the angle between the axis of tip 56 and central axis 60. FIG. 2C shows a spatula 30 with a bend angle $\theta_{blade}=0$ and a blade angle $\theta_{blade}=0$. FIG. 2D shows a top view of spatula 30 with blade 52 and edge 54. Blade length $L_b$ represents the length of blade 52 along center axis 60, and blade width $W_b$ represents the width of edge 54. Cross-section reference A indicates a cross section of spatula 30, which is described in more detail with reference to FIG. 2E.

Spatula 30 may have any suitable size or shape. Blade width $W_b$ may have any suitable value, for example, in the range of 0.2 millimeters (mm) to 0.8 mm. Blade length $L_b$ may have any suitable value, for example, in the range of 1 mm to 10 mm. Tip thickness $T_t$ may have any suitable value, for example, in the range of 0.3 to 2 mm, such as 1.2 to 1.7 mm.

Bend angle $\theta_{bend}$ may have any suitable value, for example, in the range of 0 to 30 degrees, such as 0 to 15 degrees. Blade angle $\theta_{blade}$ may have any suitable value, for example, in the range of 20 to 60 degrees. Tip angle $\theta_{tip}$ may have any suitable value, for example, in the range of 20 to 70 degrees.

Figure 2E:
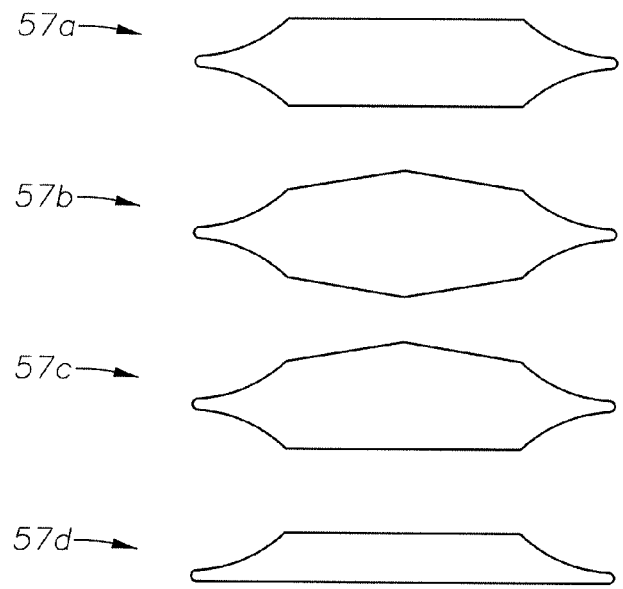

FIG. 2E illustrates examples of a cross-section 57(57*a-d*) of spatula 30 along cross-section reference A of FIG. 2D. Cross-section 57*a* has flat upper and lower surfaces; cross-section 57*b* has beveled upper and lower surfaces; cross-section 57*c* has a beveled upper surface and a flat lower surface; and cross-section 57*d* has an asymmetric upper surface and a flat lower surface.

Figure 2F:
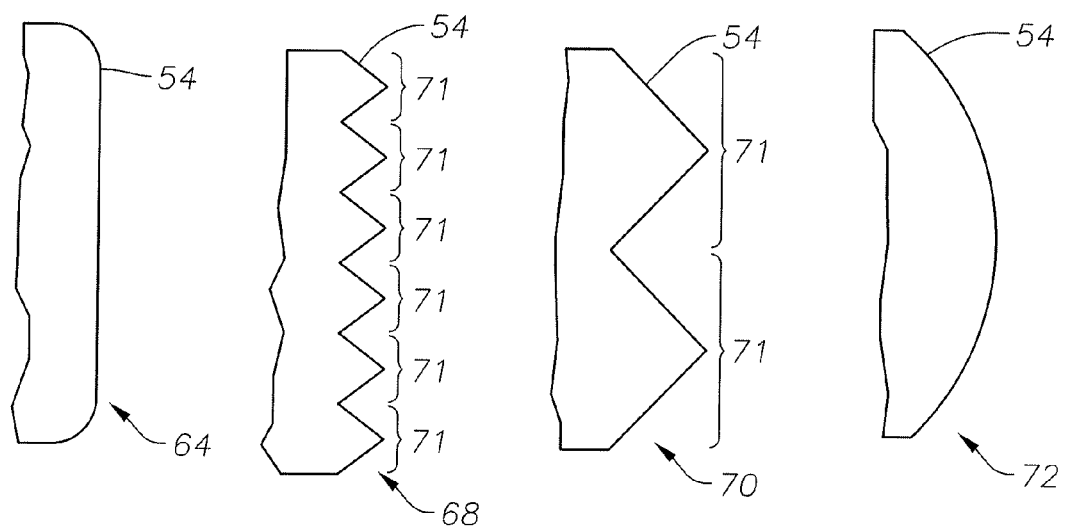

FIG. 2F illustrates examples of edges 54 of spatula 30. Straight edge 64 is substantially straight and may have corners that are rounded or right angles. Serrated edges 68 and 70 may have any suitable number of serrations 71, e.g., 1 through 20 serrations. Serrated edge 68 has six serrations 71, and serrated edge 70 has two serrations. Curved edge 70 may have any suitable curvature, such as almost flat to semicircular.

Figure 3:
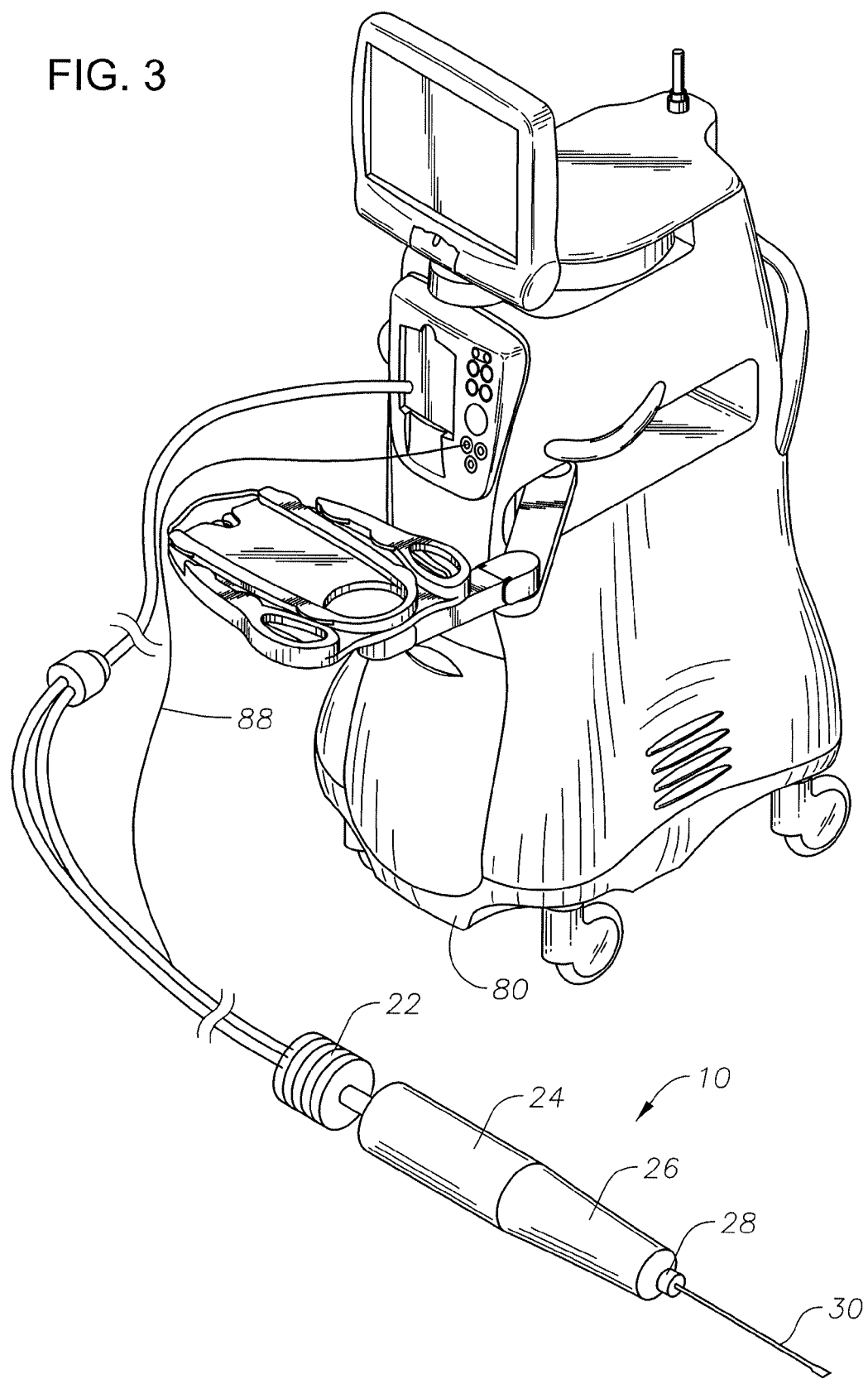
FIG. 3 illustrates an example of a surgical console that may be used with an ultrasonic handpiece according to certain embodiments.

FIG. 3 illustrates an example of a surgical console 80 that may be used with handpiece 10. Surgical console 80 may be any suitable surgical console 80, such as the INFINITI surgical systems available from ALCON LABORATORIES, INC., Fort Worth, Tex. Surgical console 80 is coupled to handpiece 10. Power is supplied to handpiece through electrical cable 88.

Figure 4:
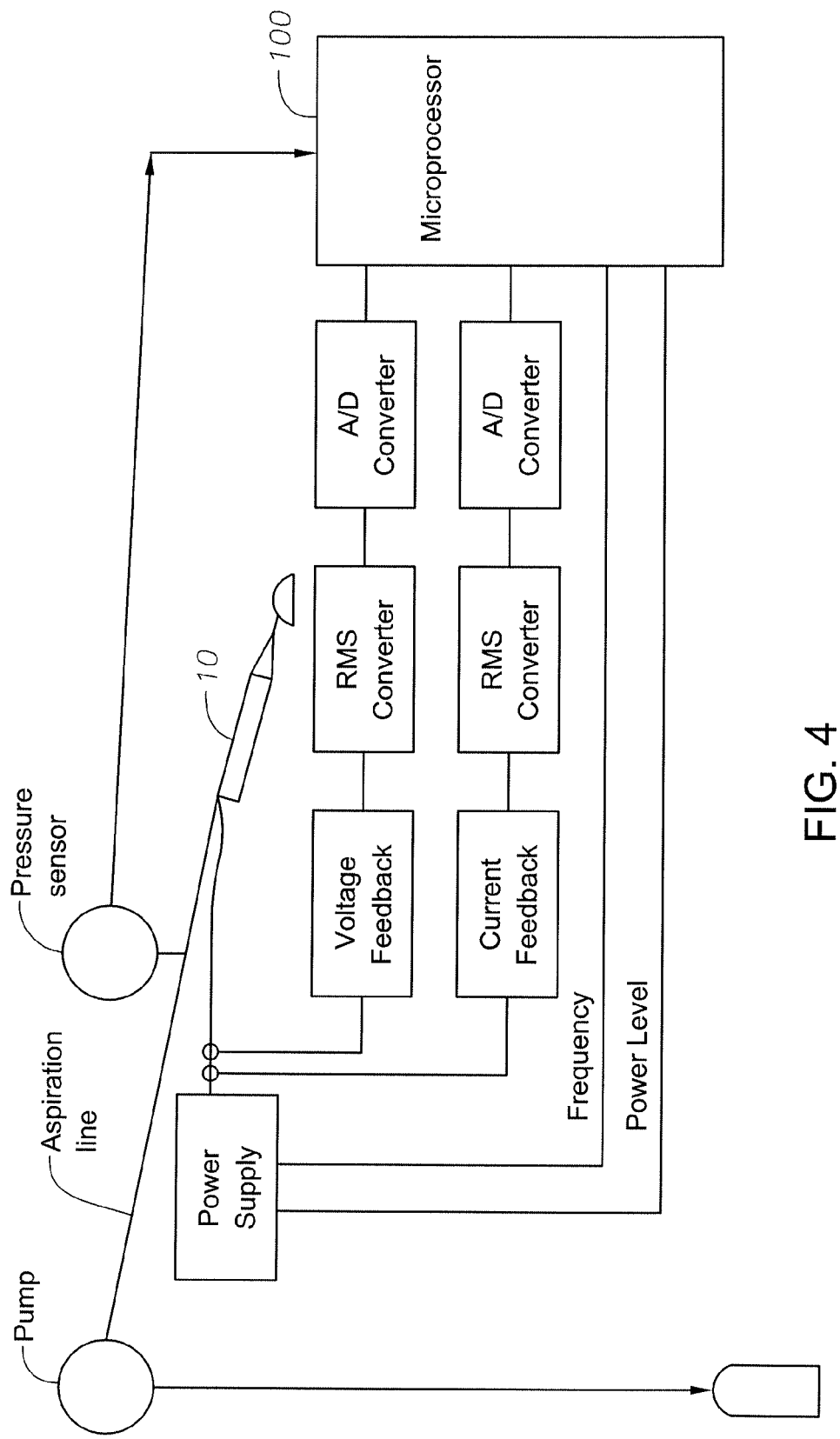
FIG. 4 illustrates an example of a drive circuit that may be used with an ultrasonic handpiece according to certain embodiments.

FIG. 4 illustrates an example of drive circuit 100 that may be used with handpiece 10. Examples of drive circuit 100 are described in U.S. Pat. No. 5,431,664, the entire contents of which being incorporated herein by reference. In certain embodiments, drive circuit 100 tracks admittance of handpiece 10 and controls the frequency of handpiece 10 to maintain a constant admittance. Drive circuit 100 may monitor the torsional mode and/or the longitudinal mode and controls these modes in handpiece 10 using different drive frequencies depending upon the piezoelectric elements and horn 12. In certain embodiments, the torsional drive signal is approximately 32 kHz and the longitudinal drive signal is approximately 44 kHz. One or more drive signals may be continuous or they may be alternated. For example, the drive signal may be provided in a desired pulse at one frequency and then switched to the other frequency for a similar pulse, with no overlap between the frequencies. There may be short or no gaps in the drive signal. The amplitude of the drive signal may be modulated and set independently for each frequency.

A component of the systems and apparatuses disclosed herein (such as surgical console 80) may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:
1. A handpiece system comprising:
an ultrasonic handpiece comprising:
    a vibration source configured to produce a plurality of ultrasonic vibrations; and
    a horn configured to transform the vibrations into ultrasonic motion; and
a spatula coupled to the horn and configured to move according to the ultrasonic motion, the spatula comprising a spatula handle having a central axis and a blade, the blade comprising a proximal portion extend- ing from a distal end of the spatula handle and a blade tip extending from a distal end of the proximal portion, wherein:
   a central axis of the proximal portion has an angle ($\theta_{bend}$) that is greater than zero and less than 30 degrees relative to the central axis of the spatula handle;
   a central axis of the blade tip has an angle ($\theta_{blade}$) between 20 degrees and 60 degrees relative to the central axis of the spatula handle; and
   the angle between opposing surfaces of the blade tip ($\theta_{tip}$) is between 20 degrees and 70 degrees.

2. The handpiece system of claim 1, the ultrasonic motion comprising a longitudinal motion.

3. The handpiece system of claim 1, the ultrasonic motion comprising a torsional motion.

4. The handpiece system of claim 1, the spatula having a blade width of 0.2 millimeters (mm) to 0.8 mm.

5. The handpiece system of claim 1, the spatula having a blade length of 1 mm to 10 mm.

6. The handpiece system of claim 1, the spatula having a curved edge.

7. The handpiece system of claim 1, the spatula having a serrated edge.

8. The handpiece system of claim 1, the spatula having a cross-section with a beveled upper surface and a flat lower surface.

9. The handpiece system of claim 1, the spatula having a cross-section with a beveled upper surface and a beveled lower surface.

10. The handpiece system of claim 1, the spatula having a cross-section with an asymmetric upper surface and a flat lower surface.

11. A method comprising:
   producing, by a vibration source of an ultrasonic handpiece, a plurality of ultrasonic vibrations;
   transforming, by a horn coupled to the vibration source, the vibrations into ultrasonic motion; and
   moving a spatula coupled to the horn with the ultrasonic motion, the spatula comprising a spatula handle having a central axis and a blade, the blade comprising a proximal portion extending from a distal end of the spatula handle and a blade tip extending from a distal end of the proximal portion, wherein:
      a central axis of the proximal portion has an angle ($\theta_{bend}$) that is greater than zero and less than 30 degrees relative to the central axis of the spatula handle;
      a central axis of the blade tip has an angle ($\theta_{blade}$) between 20 degrees and 60 degrees relative to the central axis of the spatula handle; and
      the angle between opposing surfaces of the blade tip ($\theta_{tip}$) is between 20 degrees and 70 degrees.

12. The method of claim 11, the ultrasonic motion comprising a longitudinal motion.

13. The method of claim 11, the ultrasonic motion comprising a torsional motion.

* * * * *